United States Patent [19]
Lukase et al.

[11] Patent Number: 5,378,151
[45] Date of Patent: * Jan. 3, 1995

[54] DENTAL PROSTHETIC EXTRACTING TOOL

[75] Inventors: Stephen P. Lukase, Sun City West, Ariz.; Thomas A. Lukase, 267 Greentree La., La Jolla, Calif. 92037

[73] Assignee: Thomas A. Lukase, La Jolla, Calif.

[ * ] Notice: The portion of the term of this patent subsequent to Jun. 8, 2010 has been disclaimed.

[21] Appl. No.: 1,320

[22] Filed: Jan. 7, 1993

Related U.S. Application Data

[63] Continuation of Ser. No. 786,296, Nov. 1, 1991, Pat. No. 5,217,371.

[51] Int. Cl.⁶ ............................ A61C 3/08; A61C 3/00
[52] U.S. Cl. ................................... 433/150; 433/141
[58] Field of Search ............... 433/141, 146, 147, 150, 433/151

[56] References Cited

U.S. PATENT DOCUMENTS

| | | | |
|---|---|---|---|
| 2,016,597 | 10/1935 | Drake | 433/142 X |
| 2,776,490 | 1/1957 | Carfagni | 433/151 |
| 2,937,446 | 5/1960 | Weisenfeld | 433/147 X |
| 3,562,912 | 2/1971 | Edelman | 433/150 X |
| 3,645,255 | 2/1972 | Robinson | 433/119 X |
| 3,660,902 | 5/1972 | Axelsson | 433/142 |
| 3,686,756 | 8/1972 | Pankratz | 433/151 |
| 3,690,005 | 9/1972 | Edelman | 433/150 X |
| 3,702,028 | 11/1972 | Edelman | 433/150 |
| 4,195,625 | 4/1980 | Bukowski | 433/147 X |
| 4,283,174 | 8/1981 | Sertich | 433/119 |
| 5,217,371 | 6/1993 | Lukase | 433/150 |

FOREIGN PATENT DOCUMENTS 2743067  3/1979  Germany ........................ 433/150

Primary Examiner—Paul J. Hirsch
Assistant Examiner—Nicholas D. Lucchesi
Attorney, Agent, or Firm—Cahill, Sutton & Thomas

[57] ABSTRACT

An attachment tip for use with a slide hammer includes a straight foot bent extending at an angle of 90° to the body of the tip. The foot is adapted to engage and impart percussive forces to a dental prosthetic without causing damage in the nature of breakage or bending. In a variant foot, inserts, specially configured to mate with a component of the dental prosthetic device, are detachably detachable to the foot of the tip.

13 Claims, 1 Drawing Sheet

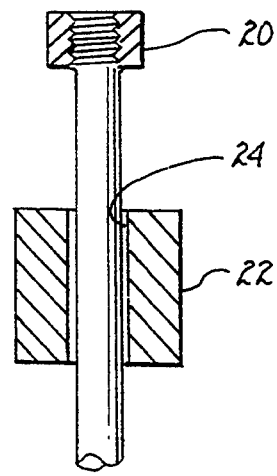
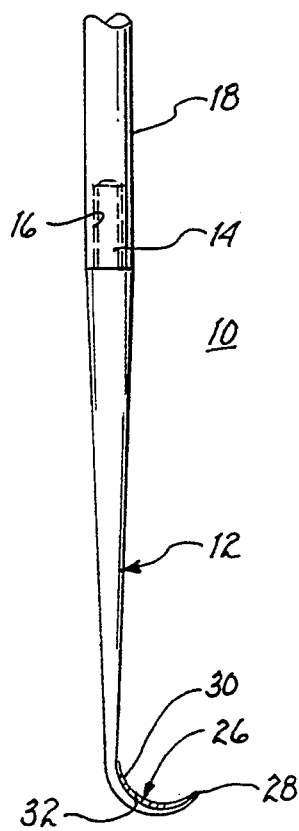
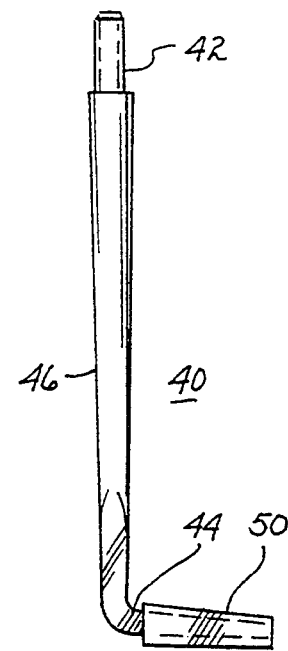
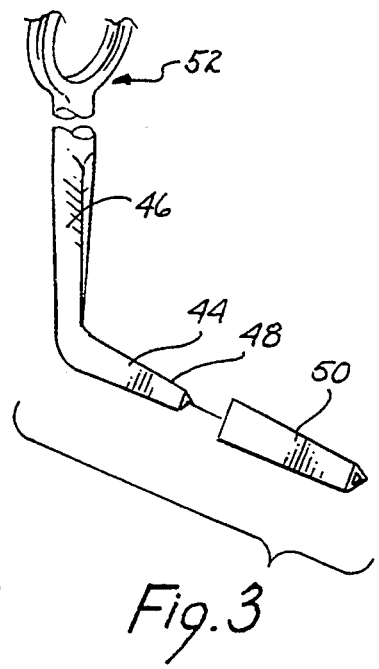
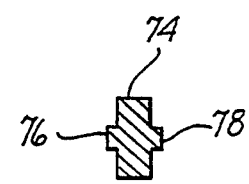
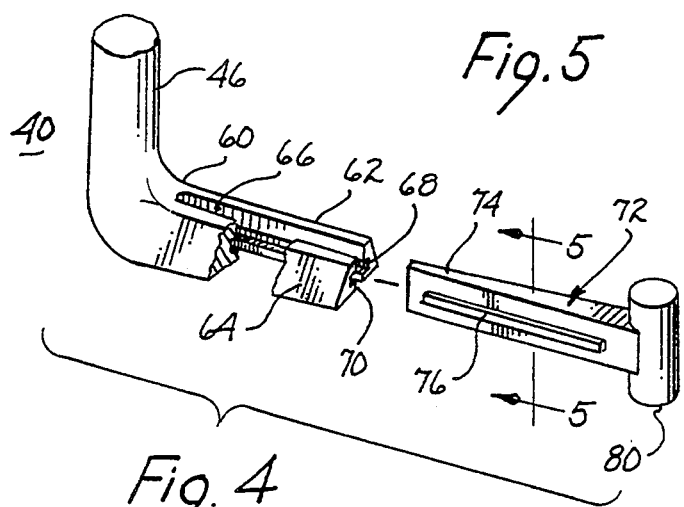
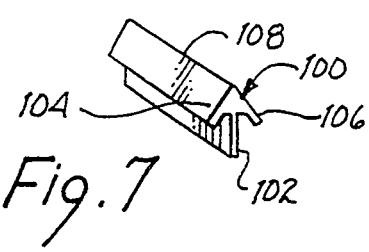
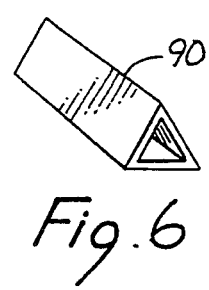

DENTAL PROSTHETIC EXTRACTING TOOL

This application is a continuation application Ser. No. 07/786,296 of a copending application entitled "Dental Prosthetic Extracting Tool", filed Nov. 1, 1991, now U.S. Pat. No. 5,217,371 describing an invention by the present inventors and assigned to the present assignee.

BACKGROUND OF THE INVENTION

1. Field of the Invention

The present invention relates to dental extraction tools and, more particularly, to slide hammer operated extraction tools for use with dental prosthetic devices.

2. Description of Related Art

From time to time, dental prosthetics must be removed by a dentist because of damage to the dental prosthetic, deterioration or breakage of the supporting tooth structure, injury to the oral cavity and for other reasons. Where the dental prosthetic is a bridge, a section of the bridge is usually engaged by a tool for the purpose of applying a force to pull or draw the bridge off the supporting tooth structure. Experience over many decades suggests that the most effectively applied force is one generated by a dental slide hammer. Such a device generally includes a rod upon which a weight may be slid. By sliding the weight with greater or lesser force to one end of the hammer, it will come in contact with a stop. The force of the impact is translated from the stop through the rod and to the dental prosthetic device engaged. Thus, a force of controllable magnitude is applied. The result of the impact force applied will generally break the adhering bonds retaining the dental prosthetic in place. Once the bonds have been broken, complete removal is readily effected by gripping and manipulation with conventional dental forceps.

The most commonly used tips detachably detachable to a slide hammer mechanism are sickle or "J" shaped. The foot is generally curved toward the slide hammer to serve in the manner of a hook to grip a segment of the dental prosthetic. To permit substantial penetration of the dental prosthetic the foot is often tapered and terminates at a sharp point. The cross section of the foot may be circular or teardrop shaped with the upper side of the foot defining a sharp edge.

Because of the curvature of the hook of a conventional extracting tool tip, engagement of the dental prosthetic is relatively easy. Furthermore, because the tip may be oriented through a wide range of angles while still bearing against an element of the dental prosthetic, manipulation of the attached slide hammer is facilitated. The major problem attendant extracting tools of this type relates to the damage and/or bending usually done to the dental prosthetic during extraction. When a tip includes a sharp edge in engagement with the dental prosthetic, nicking (and thereby weakening) or actual cutting of an element of the dental prosthetic may occur during imposition of the impact force(s).

The generally anticipated and resulting damage or deformation of the dental prosthetic requires either repair or replacement which is costly to the patient and time consuming for the dentist. In situations where the dental prosthetic is to be discarded, such damage is of no consequence. In most instances, extraction is made for purposes of adjustment or reattachment and maintenance of the integrity of the dental prosthetic device is important.

SUMMARY OF THE INVENTION

An extraction tool, threadedly or otherwise engageable with a slide hammer, includes a foot extending approximately 90° to the longitudinal axis of the tool. The foot may be configured to receive and support any of a plurality of attachments. These attachments are specially configured as a function of the part of a dental prosthetic to be engaged or as a function of the degree of modification of the impact force to be applied to the dental prosthetic device. In a variant of the foot, any of a plurality of different inserts may be slideably engaged with and retained by the foot. Each of these inserts provides a particularly configured surface or configuration to engage and/or bear against a particular element(s) of a dental prosthetic to apply the impact forces exerted by the slide hammer without consequential breakage or deformation of the contacted element(s).

It is therefore a primary object of the present invention to provide a non-damaging tip for a dental prosthetic extraction tool.

Another object of the present invention is to provide a dental prosthetic engaging foot of an extraction tool which corresponds with the element to be engaged to minimize damage thereto.

Still another object of the present invention is to provide a proper geometric fit of the foot of an impact tool in the inner proximal area of a dental prosthetic.

Still another object of the present invention is to provide a foot of a dental prosthetic impact tool which is modifiable in shape to conform with the dental prosthetic device to be removed.

A further object of the present invention is to provide a foot of a impact tool which is mateable with each of a plurality of inserts configured for engagement with a particularly shaped element of a dental prosthetic device.

A yet further object of the present invention is to provide variously configured inserts for use with a foot of a dental impact tool for the purpose of remaining a dental prosthetic device.

A still further object of the present invention is to provide a method for removing dental prosthetic devices without damage.

These and other objects of the present invention will become apparent to those skilled in the art as the description there of proceeds.

BRIEF DESCRIPTION OF THE DRAWINGS

The present invention will be described with greater specificity and clarity with reference to the following drawings, in which:

FIG. 1 is a partial cut-away view of a prior art extraction tool attached to a slide hammer;

FIG. 2 is a side view of an extraction tool tip attachable to a slide hammer;

FIG. 3 is an isometric view illustrating a sleeve engaging the foot of the extraction tool;

FIG. 4 is a partial cut-away view illustrating a variant of a foot and an insert usable therewith;

FIG. 5 is a cross-sectional view taken along lines 5—5, shown in FIG. 4;

FIG. 6 is an isometric view illustrating a sleeve usable with the foot of the impact tool; and FIG. 7 illustrates a further insert usable in conjunction with the foot shown in FIG. 4.

DESCRIPTION OF THE PREFERRED EMBODIMENT

Impact tools for extracting dental prosthetic devices by manipulation of an attached slide hammer have been used in the field of dentistry for decades. Referring to FIG. 1, there is shown a representative version of such an impact tool 10 presently commercially available. The tool includes a tip 12 having a threaded shank 14 in threaded engagement with a threaded cavity 16 disposed at one end of rod 18. The rod includes an end cap 20 threadedly or otherwise rigidly secured to the rod. A cylinder 22 includes a central passageway 24 for penetrably receiving rod 18. Preferably, the cylinder is of steel in order to be of relatively massive weight and not readily deformable upon impact with end cap 20.

Tip 12 includes an upturned portion or hook 26 disposed at one end. Usually, the hook is tapered to a sharp point 28. The cross-section of the hook may be round or teardrop shaped, as is more conventional. Interior edge 30 corresponds with the upper extremity of the teardrop shape and is relatively sharp. Alternatively, edge 30 may be defined by a pair of intersecting beveled surfaces, of which surface 32 is shown.

In operation, hook 26 is brought into penetrable engagement with a dental prosthetic, such as a bridge, to be removed. Sharp point 28 permits insertion in narrow spaces or confines of the bridge. Preferably, edge 30 is brought to bear against an element of the bridge, which element will receive the impact force applied. The impact force is applied by rapidly sliding cylinder 26 toward end cap 20. Upon contact with the end cap, a force, in general alignment with the longitudinal axis of rod 18, is exerted upon the end cap. This force is translated through the rod to edge 30 in contact with an element of the bridge. The sharp impact force acting upon the bridge will tend to break the adhesion or other attachment mechanism with which the bridge is secured in place. Repeated impact forces may be applied, as necessary, by repetitive sliding movements of cylinder 22 against end cap 20. After the bridge has been broken loose, removal can be effected with dental forceps.

Because of the generalized nature of hook 26, it will fit most bridges. However, the point of contact with the bridge may be insufficient to withstand the impact force without breakage or deformation of the bridge; this is the usual situation. As a result, repair or reconstruction of the bridge must be performed to repair the damage or breakage that occurred during removal. Such additional work is expensive for the patient and time consuming for the dentist. The use of a sharp edge 30 as the surface transmitting the impact force to the dental prosthetic will have a tendency to nick or even cut through the element contacted. Such damage must necessarily be repaired prior to reinstallation of the bridge.

FIG. 2 illustrates a tip 40 having a threaded shank 42 for engagement with a slide hammer, such as that shown in FIG. 1. Other means for attachment with the same or different types of slide hammers could also be used. The anterior end of the tip includes a foot 44 extending from body 46 of the tip and at an angle of approximately ninety degrees (90°) to the longitudinal axis of the tip. Preferably, the foot is tapered as shown. Under most circumstances, the taper should not terminate in a sharp point and the taper should be truncated, as shown. The use of the resulting straight edge, or surface, permits application of the impact force to a single element of the dental prosthetic, if desired, or to two or more elements simultaneously to divide the impact force therebetween. In the event of the existence of a ledge or other elongated surface contactible by the foot, the impact force can be spread there along by placing the foot adjacent such surface. It will therefore become readily apparent that the impact force, is applied in totality to the dental prosthetic device but distributed there along. Distribution of the impact force will create a lower probability of damage or deformation to the dental prosthetic device at the point of contact.

As shown in FIG. 3, foot 44 may be triangular in cross-section to include a relatively sharp edge 48. This sharp edge is sometimes useful for applying the impact force at the junction of two or more elements of a dental prosthetic or at a particular convolution attendant the dental prosthetic device. To ameliorate the likelihood of nicking or cutting the dental prosthetic device, a sleeve 50 may be slid over foot 44, as shown in FIG. 2. This sleeve may be of material soft enough to deform prior to deformation of the dental prosthetic device. Since the sleeve is replaceable ad easily disposable, damage to it is of no consequence. Thereby, relatively substantial impact forces can be applied through a slide hammer attached to tip 40 without fear of damage to the dental prosthetic device since any damage that may occur will be limited to damage of sleeve 50.

The conventional manner for attaching a tip with a slide hammer is a threaded shank, such as threaded shank 42 shown in FIG. 2. To provide greater manipulative freedom during engagement and disengagement between a tip and a slide hammer, a loop 52 may be formed at the end of the tip, as shown in FIG. 3. This loop can be engaged by an appropriately formed hook or the like, in the slide hammer. The loop may be rigid and formed as part of the tip or it may be a flexible cable or other element permanently or detachably attached to the tip. By using two or more tips with loops located at different parts of a dental prosthetic device to assist in removing the dental prosthetic device, a single slide hammer can be quickly moved from one tip to the other tip to provide differently oriented impact forces and to facilitate removal of the dental prosthetic device.

Referring to FIG. 4, there is shown a variant 60 depicting a split foot 44 and extending from body 46 of tip 40. Prongs 62,64 of variant 60 are separated from one another by a channel 66. Prongs 62,64 may include grooves 68,70 opening toward one another within channel 66. These grooves may be tapered or constant depth. A wedge 72 includes a tongue 74 slidable within channel 66. The tongue may include tenons 76,78 (see also FIG. 5). The tenons slidingly mate with respective ones of grooves 68,70. The wedge may include an expanded element 80 disposed at the end thereof for ease in manipulating the wedge. Furthermore, the expanded element can be used to lock foot 60 within the dental prosthetic device under certain circumstances. To accomplish this end, the foot is first brought into engagement with the dental prosthetic device. The wedge is then engaged with the foot and frictionally locked in place through manipulation of expanded element 80. The expanded element, if appropriately dimensioned, will prevent inadvertent withdrawal of the foot. Moreover, it may be of assistance in manipulating tip 40 prior to application of the impact forces.

Foot 60 may include prong 62 and 64 of a tapered configuration, similar to the plan form of the foot shown in FIG. 3. Wedge 72 may thereafter be used to expand the foot to lock it in place or to more firmly position it within the dental prosthetic. Alternatively, prong 62,64 may be non tapered or even reverse tapered, with subsequent expansion upon engagement of wedge 72, such variations are a function of the nature and construction of the dental prosthetic to be removed. As illustrated in FIG. 4, each of prong 62,64 has a cross-section resembling a truncated right triangle. In concert, these prongs define in cross-section a trapezoid or a truncated triangle.

Referring to FIG. 6, there is illustrated a triangular sleeve 90 which may be of material more soft than that of the dental prosthetic. This sleeve is matingly slidable upon foot 60 to ensure that any damage due to the impact forces be absorbed by the sleeve and not the dental prosthetic. Under some circumstances, sleeve 90 may be of a rubber composition or of synthetic material which is intended to compress in the direction of the applied force and expand laterally to provide a greater surface area through which the impact force is applied.

FIG. 7 illustrates an insert 100 to be supported upon foot 60. It includes a depending flange 102 for insertion within channel 66. Sloping sides 104,106 rest against the upper surfaces of prong 62,64 and define a relatively sharp edge 108. Upon attachment of insert 100, the resulting cross-section of foot 60 is essentially triangular, as shown in FIG. 3. It is to be noted that sleeve 90, shown in FIG. 6, may be slid over foot 60 with insert 100 attached.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A tool for engaging and applying a force to remove a dental prosthetic device, said tool comprising in combination:
    a) a body having a longitudinal axis;
    b) a linear split foot having a longitudinal axis and extending essentially perpendicularly from said body, said split foot including a pair of free ends for engaging the dental prosthetic device, said split foot including a pair of prongs defining said pair of free ends, each of said prongs having a lateral cross-section transverse to the longitudinal axis of said split foot and defining essentially a truncated right triangle; and
    c) said body including means for applying the force to said body along its longitudinal axis to remove the dental prosthetic device.

2. The tool as set forth in claim 1 including a longitudinally oriented groove disposed in each of said prongs, said grooves being oriented in opposed facing relationship with one another and a wedge for engaging said grooves.

3. The tool as set forth in claim 2 wherein said wedge includes a tongue engageable with said pair of prongs for retaining said wedge in place.

4. The tool as set forth in claim 1 including a wedge for engaging said prongs, said wedge having a longitudinal axis in general alignment with said foot.

5. The tool as set forth in claim 4 wherein said wedge includes an expanded element displaced from said foot for engaging the dental prosthetic device.

6. The tool as set forth in claim 5 including means for retaining longitudinal alignment of said wedge with said foot upon engagement of said wedge with said prongs.

7. The tool as set forth in claim 1 including an insert insertable intermediate said prongs for converting the lateral cross-section of said foot to a triangle.

8. The tool as set forth in claim 7 wherein said insert includes a sleeve, said sleeve being deformable for engaging and without damaging the dental prosthetic device.

9. The tool as set forth in claim 7 wherein said insert includes an edge extending longitudinally along said foot.

10. The tool as set forth in claim 1 wherein said foot tapers linearly from said body.

11. A tool for engaging and applying a force to remove a dental prosthetic device, said tool comprising in combination:
    a) a body having a longitudinal axis;
    b) a linear split foot having a longitudinal axis and extending essentially perpendicularly from said body, said split foot including a pair of free ends for engaging the dental prosthetic device, said split foot including a pair of spaced apart prongs for defining said pair of free ends;
    c) an insert located intermediate and retained by said pair of prongs for assisting in engaging the dental prosthetic device; and
    d) said body including means for applying the force to said body along its longitudinal axis to remove the dental prosthetic device.

12. The tool as set forth in claim 11 wherein said pair of prongs, in combination with said insert, define a longitudinally oriented edge for engaging the dental prosthetic device.

13. A tool for engaging a dental prosthetic device and for applying a force to remove the dental prosthetic device, said tool comprising in combination:
    a) a body having a longitudinal axis;
    b) a linear foot extending from said body for engaging the dental prosthetic device, said foot having a longitudinal axis extending from said body and a lateral cross-section tapering in at least one lateral dimension transverse to the longitudinal axis of said foot and defining three converging extending edges, at least one of said extending edges being oriented to contact the dental prosthetic device upon applying a force to said body along the longitudinal axis of said body to remove the dental prosthetic; and
    c) a sleeve extending along said foot and encircling said foot for protecting the dental prosthetic device from damage due to impact forces and loads that may be imposed by said foot, said sleeve including a longitudinal axis aligned with said foot and a lateral axis, said sleeve having a triangular cross-section in the lateral axis and transverse to the longitudinal axis of said sleeve.

* * * * *